(12) United States Patent
Linderman et al.

(10) Patent No.: US 9,526,551 B2
(45) Date of Patent: *Dec. 27, 2016

(54) APPARATUS AND METHOD FOR STYLET-GUIDED VERTEBRAL AUGMENTATION

(71) Applicant: Stryker Corporation, Kalamazoo, MI (US)

(72) Inventors: Evan D. Linderman, Deerfield, IL (US); John A. Krueger, Muskego, WI (US)

(73) Assignee: STRYKER CORPORATION, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/873,947

(22) Filed: Oct. 2, 2015

(65) Prior Publication Data

US 2016/0022343 A1 Jan. 28, 2016

Related U.S. Application Data

(63) Continuation of application No. 14/528,384, filed on Oct. 30, 2014, now Pat. No. 9,168,078, which is a continuation of application No. 13/483,919, filed on May 30, 2012, now Pat. No. 8,894,658, which is a continuation-in-part of application No. 12/615,573, filed on Nov. 10, 2009, now Pat. No. 8,226,657, said application No. 14/528,384 is a continuation-in-part of application No. 14/050,017, filed on Oct. 9, 2013, now (Continued)

(51) Int. Cl.
*A61B 17/88* (2006.01)
*A61B 17/16* (2006.01)
*A61B 17/00* (2006.01)

(52) U.S. Cl.
CPC ....... *A61B 17/8819* (2013.01); *A61B 17/1642* (2013.01); *A61B 17/8805* (2013.01); *A61B 17/8811* (2013.01); *A61B 17/8822* (2013.01); *A61B 17/8855* (2013.01); *A61B 2017/00867* (2013.01); *A61B 2090/062* (2016.02); *A61B 2090/0811* (2016.02); *A61B 2090/3966* (2016.02)

(58) Field of Classification Search
CPC ............ A61B 17/8802; A61B 17/8805; A61B 17/8811; A61B 17/8816; A61B 17/8852
See application file for complete search history.

(56) References Cited

U.S. PATENT DOCUMENTS

| | | | |
|---|---|---|---|
| 4,265,231 A | 5/1981 | Scheller, Jr. et al. |
| 4,969,888 A | 11/1990 | Scholten et al. |

(Continued)

FOREIGN PATENT DOCUMENTS

| | | |
|---|---|---|
| EP | 1459691 A1 | 9/2004 |
| WO | WO 98/56301 A1 | 12/1998 |

*Primary Examiner* — Anu Ramana
(74) *Attorney, Agent, or Firm* — Howard & Howard Attorneys PLLC

(57) ABSTRACT

A stylet-guided balloon vertebroplasty system, as well as methods for bone augmentation using same are provided. In certain embodiments, a pre-curved stylet with an overlying delivery tube may be used to target an approximately centered target site within a bone structure, facilitating direction thereto of an expandable member useful for creating a cavity that may receive curable material to restore bone height and/or to reinforce the bone structure.

20 Claims, 16 Drawing Sheets

Related U.S. Application Data

Pat. No. 9,095,393, and a continuation-in-part of application No. 14/223,064, filed on Mar. 24, 2014, now Pat. No. 9,358,059, which is a continuation-in-part of application No. 13/483,899, filed on May 30, 2012, now Pat. No. 8,690,884.

(56) References Cited

U.S. PATENT DOCUMENTS

| | | |
|---|---|---|
| 5,106,376 A | 4/1992 | Mononen et al. |
| 5,295,980 A | 3/1994 | Ersek |
| 5,512,051 A * | 4/1996 | Wang ............... A61M 25/0045 604/101.02 |
| 5,609,629 A | 3/1997 | Fearnot et al. |
| 5,732,698 A | 3/1998 | Swanson et al. |
| 5,800,378 A | 9/1998 | Edwards et al. |
| 5,843,103 A | 12/1998 | Wulfman |
| 5,851,209 A | 12/1998 | Kummer et al. |
| 5,879,353 A | 3/1999 | Terry |
| 5,891,147 A | 4/1999 | Moskovitz et al. |
| 5,928,239 A | 7/1999 | Mirza |
| 5,972,015 A | 10/1999 | Scribner et al. |
| 6,019,776 A | 2/2000 | Preissman et al. |
| 6,033,411 A | 3/2000 | Preissman |
| 6,048,346 A | 4/2000 | Reiley et al. |
| 6,066,154 A | 5/2000 | Reiley et al. |
| 6,241,734 B1 | 6/2001 | Scribner et al. |
| 6,248,110 B1 | 6/2001 | Reiley et al. |
| 6,296,639 B1 | 10/2001 | Truckai et al. |
| 6,328,744 B1 | 12/2001 | Harari et al. |
| 6,358,251 B1 | 3/2002 | Mirza |
| 6,383,188 B2 | 5/2002 | Kuslich et al. |
| 6,383,190 B1 | 5/2002 | Preissman |
| 6,425,887 B1 | 7/2002 | McGuckin et al. |
| 6,440,138 B1 | 8/2002 | Reiley et al. |
| 6,494,868 B2 | 12/2002 | Amar |
| 6,569,179 B2 | 5/2003 | Teoh et al. |
| 6,575,978 B2 | 6/2003 | Peterson et al. |
| 6,592,559 B1 | 7/2003 | Pakter et al. |
| 6,641,587 B2 | 11/2003 | Scribner et al. |
| 6,645,213 B2 | 11/2003 | Sand et al. |
| 6,676,664 B1 | 1/2004 | Al Assir |
| 6,679,886 B2 | 1/2004 | Weikel et al. |
| 6,740,090 B1 | 5/2004 | Cragg et al. |
| 6,746,451 B2 | 6/2004 | Middleton et al. |
| 6,783,515 B1 | 8/2004 | Miller et al. |
| 6,790,210 B1 | 9/2004 | Cragg et al. |
| 6,793,660 B2 | 9/2004 | Kerr et al. |
| 6,814,734 B2 | 11/2004 | Chappuis et al. |
| 6,843,796 B2 | 1/2005 | Harari et al. |
| 6,863,672 B2 | 3/2005 | Reiley et al. |
| 6,875,219 B2 | 4/2005 | Arramon et al. |
| 6,921,403 B2 | 7/2005 | Cragg et al. |
| 6,923,813 B2 | 8/2005 | Phillips et al. |
| 7,004,945 B2 | 2/2006 | Boyd et al. |
| 7,025,771 B2 | 4/2006 | Kuslich et al. |
| 7,048,743 B2 | 5/2006 | Miller et al. |
| 7,066,942 B2 | 6/2006 | Treace |
| 7,087,040 B2 | 8/2006 | McGuckin, Jr. et al. |
| 7,087,058 B2 | 8/2006 | Cragg |
| 7,114,501 B2 | 10/2006 | Johnson et al. |
| 7,682,378 B2 | 3/2010 | Truckai et al. |
| 7,713,273 B2 | 5/2010 | Krueger et al. |
| 7,799,035 B2 | 9/2010 | Krueger et al. |
| 7,922,690 B2 | 4/2011 | Plishka et al. |
| 8,128,633 B2 | 3/2012 | Linderman et al. |
| 8,226,657 B2 | 7/2012 | Linderman et al. |
| 8,419,730 B2 | 4/2013 | Pellegrino et al. |
| 8,529,576 B2 | 9/2013 | Krueger et al. |
| 8,690,884 B2 | 4/2014 | Linderman et al. |
| 8,771,278 B2 | 7/2014 | Linderman et al. |
| 9,168,078 B2 * | 10/2015 | Linderman ........ A61B 17/8805 |
| 2002/0099384 A1 | 7/2002 | Scribner et al. |
| 2002/0120240 A1 | 8/2002 | Bagga et al. |
| 2002/0156483 A1 | 10/2002 | Voellmicke et al. |
| 2003/0036762 A1 | 2/2003 | Kerr et al. |
| 2003/0078589 A1 | 4/2003 | Preissman |
| 2004/0068264 A1 | 4/2004 | Treace |
| 2004/0068267 A1 | 4/2004 | Harvie et al. |
| 2004/0162559 A1 | 8/2004 | Arramon et al. |
| 2004/0215202 A1 | 10/2004 | Preissman |
| 2005/0038432 A1 | 2/2005 | Shaolian et al. |
| 2005/0070913 A1 | 3/2005 | Milbocker et al. |
| 2006/0009779 A1 | 1/2006 | Collins et al. |
| 2006/0064101 A1 | 3/2006 | Arramon |
| 2006/0116643 A1 | 6/2006 | Dixon |
| 2006/0149280 A1 | 7/2006 | Harvie et al. |
| 2006/0195094 A1 | 8/2006 | McGraw et al. |
| 2006/0217736 A1 | 9/2006 | Kaneko et al. |
| 2006/0241624 A1 | 10/2006 | Kizuka et al. |
| 2006/0264967 A1 | 11/2006 | Ferreyro et al. |
| 2011/0087828 A1 | 4/2011 | Lee et al. |
| 2011/0245926 A1 | 10/2011 | Kitchen |
| 2012/0239047 A1 | 9/2012 | Linderman et al. |
| 2012/0239050 A1 | 9/2012 | Linderman et al. |
| 2014/0046334 A1 | 2/2014 | Schaus et al. |

* cited by examiner

APPARATUS AND METHOD FOR STYLET-GUIDED VERTEBRAL AUGMENTATION

CROSS-REFERENCE TO RELATED APPLICATIONS

Pursuant to 35 U.S.C. §120, this application is a continuation of and claims priority to and through U.S. patent application Ser. No. 14/528,384, filed Oct. 30, 2014, which is a continuation of (i) U.S. patent application Ser. No. 13/483,919, filed May 30, 2012, issued as U.S. Pat. No. 8,894,658, which is a continuation-in-part of U.S. patent application Ser. No. 12/615,573, filed Nov. 10, 2009, issued as U.S. Pat. No. 8,226,657; is a continuation-in-part of and claims priority to (ii) U.S. patent application Ser. No. 14/050,017, filed Oct. 9, 2013, issued as U.S. Pat. No. 9,095,393; and is a continuation-in-part of and claims priority to (iii) U.S. patent application Ser. No. 14/223,064, filed Mar. 24, 2014, which is a continuation-in-part of U.S. patent application Ser. No. 13/483,899, filed May 30, 2012, issued as U.S. Pat. No. 8,690,884, each of which is incorporated by reference herein in its entirety.

TECHNICAL FIELD

Embodiments disclosed herein generally relate to systems and methods for stabilizing bone structures. More particularly, they relate to systems and methods for stabilizing, and restoring the height of, a bone structure, such as a vertebral body.

BACKGROUND

Surgical intervention of damaged or compromised bone sites has proven highly beneficial for patients, including, for example, patients with back pain associated with vertebral damage. The vertebral damage may be due to injury and/or a degenerative condition such as, for example, aging and/or osteoporosis.

Bones of the human skeletal system include mineralized tissue that may be generally categorized into two morphological groups: "cortical" bone and "cancellous" bone. Outer walls of all bones are composed of cortical bone, which is a dense, compact bone structure characterized by a microscopic porosity. Cancellous or "trabecular" bone forms the interior structure of bones. Cancellous bone is composed of a lattice of interconnected slender rods and plates known by the term "trabeculae".

During certain bone-related procedures, cancellous bone is supplemented by an injection of a palliative (or curative) material employed to stabilize the trabeculae. For example, superior and inferior vertebrae in the spine may be beneficially stabilized by the injection of an appropriate, curable material (e.g., PMMA or other bone cement or bone curable material). In other procedures, percutaneous injection of stabilization material into vertebral compression factors, by, for example, transpedicular or parapedicular approaches, has proven beneficial in relieving pain and stabilizing damaged bone sites. Such techniques are commonly referred to as vertebroplasty.

A conventional vertebroplasty technique for delivering the bone stabilizing material entails placing a cannula with an internal trocar into the targeted delivery site. The cannula and trocar are used in conjunction to pierce the cutaneous layers of a patient above the hard tissue to be supplemented, then to penetrate the hard cortical bone of the vertebra, and finally to traverse into the softer, cancellous bone underlying the cortical bone. After the assembly is positioned in the cancellous bone, the trocar may be removed, leaving the cannula in the appropriate position for delivery of curable material that will reinforce and solidify the target site.

In some instances, an effectiveness of the procedure may be enhanced by forming a cavity or void within the cancellous bone, and then depositing the curable material in the cavity. For example, a balloon or other expandable device may be initially deployed and then expanded in a particular vertebroplasty procedure sometimes referred to as kyphoplasty. This action, in turn, compresses cancellous bone and other tissue to form a cavity, and may also cause a "height" of the bone to increase. As a point of reference, vertebroplasty is a common treatment for a fractured vertebral body, and the height of a fractured vertebral body is oftentimes significantly less than a native or natural height that existed before vertebral degeneration. It has been postulated that the height of a fractured vertebral body may be restored or elevated to a near-normal state when subjected to internal expansion via a balloon or other expandable member. The mechanics of height restoration in conjunction with vertebroplasty stabilization is currently unclear at best. For example, certain techniques may employ a bipedicular approach in which two balloons are inserted into the vertebral body and inflated, resulting in an increase in height (and the cavity or cavities described above).

There exists a need in the medical device field for improved systems and methods for restoring the height of, and stabilizing, a fractured vertebral body or other bone structure. In particular, it would be desirable to provide apparatus and methods to symmetrically provide bone augmentation that stabilizes a bone structure such as a vertebra, and that may also provide some height-restoration of said bone structure.

It may be desirable to provide a system and method that provides advantages with regard to reduced complexity and reduced procedure time while maintaining advantages of dual-balloon kyphoplasty and perhaps offering superior bone-centralization and symmetry of curable material placement.

BRIEF SUMMARY

In one aspect, embodiments disclosed herein may include a stylet-guided balloon-assisted vertebroplasty system, as well as methods for bone augmentation using same. In certain embodiments, a pre-curved stylet may be used to target an approximately centered target site within a bone structure, facilitating direction thereto of an expandable member useful for creating a cavity that may receive curable material to restore bone height and/or to reinforce the bone structure.

BRIEF DESCRIPTION OF THE DRAWINGS

FIG. 4I illustrates a pre-curved delivery cannula; and

DETAILED DESCRIPTION

Figure 1:
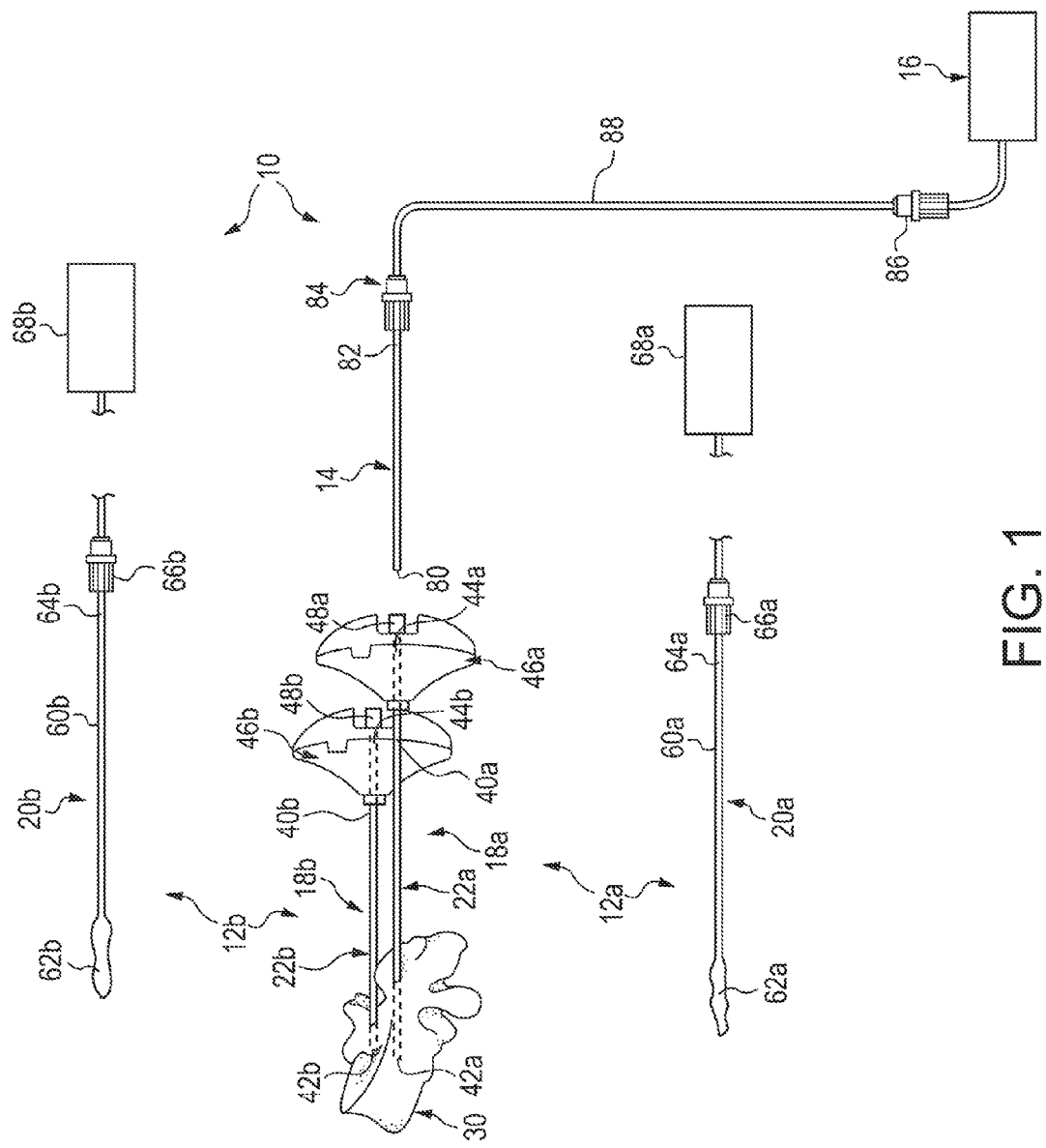
FIG. 1 is an exploded view of a curable material delivery and height restoration system, using apparatus for bipedicular access.

Embodiments are described with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

Various embodiments will be described more fully hereinafter. The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise. The word "alternatively" and its variants are used inclusively rather than exclusively (i.e., "X, alternatively, Y" means "X and/or Y" rather than "only X or only Y") unless otherwise apparent. The term "about" when used with reference to any volume, dimension, proportion, or other quantitative value is intended to communicate a definite and identifiable value within the standard parameters that would be understood by one of skill in the art (equivalent to a medical device engineer with experience in the field of vertebral augmentation and other cannular devices/systems), and should be interpreted to include at least any legal equivalents, minor but functionally-insignificant variants, and including at least mathematically significant figures.

One embodiment of a curable material delivery and height restoration system 10 is shown in FIG. 1. The system 10 includes a first delivery assembly 12a, a second delivery assembly 12b, and at least one source of curable material 16. The delivery assemblies 12a, 12b may be substantially identical, and each includes a cannula device 18a, 18b and a cavity-forming device 20a, 20b. Details on the various components are provided below. In general terms, however, the cannula devices 18a, 18b each include an access cannula 22a, 22b for insertion into a bone site of interest in a patient. In the embodiment depicted in FIG. 1, the bone site of interest is a vertebra 30. After the access cannulas 22a, 22b are desirably located relative to the vertebra 30, a portion of each of the cavity-forming devices 20a, 20b are delivered to the vertebra 30 via the corresponding access cannula 22a, 22b, and operated to form cavities. The second cavity-forming device 20b (alternatively the first cavity-forming device 20a) may be removed, and the source of curable material 16 connected to the second cannula 22b. In this regard, an delivery tube 14 may be employed, extending from the source 16 and through the second cannula 22b.

Thereafter, the curable material source 16 is operated to deliver curable material to the cavity via the second cannula 22b and/or the delivery tube 14. Subsequently, the first cavity-forming device 20a may be removed and the curable material source 16 is connected to the first cannula 22a (for example, via the delivery tube 14). The curable material source 16 is operated to deliver curable material into the corresponding cavity. With the approaches disclosed herein, the systems and methods disclosed herein will be able to provide for restore a height of the vertebra (or other bone site) 30 to a normal or near-normal state, and the delivered curable material will provide desirable stabilization.

The system 10 may be used for a number of different procedures including, for example, vertebroplasty and other bone augmentation procedures in which curable material is delivered to a site within bone (e.g., balloon-assisted procedures where a void is created by a balloon rather than by moving a needle and/or by direct displacement via injection), as well as possibly to remove or aspirate material from a site within bone. The system 10 is highly useful for delivering a curable material in the form of a bone curable material. The phrase "curable material" within the context of the substance that may be delivered by the systems and methods described herein is intended to refer to materials (e.g., composites, polymers, and the like) that have a fluid or flowable state or phase and a hardened, solid or cured state or phase.

Curable materials may include, but are not limited to, injectable bone cements (such as polymethylmethacrylate (PMMA) curable bone material), which have a flowable state wherein they may be delivered (e.g., injected) by a cannula to a site and subsequently cure into hardened, cured material. Other materials such as calcium phosphates, bone in-growth materials, antibiotics, proteins, etc., may be used in place of, or to augment bone cement (but do not affect an overriding characteristic of the resultant formulation having a flowable state and a hardened, solid, or cured state). This would allow the body to reabsorb the curable material and/or improve the clinical outcome based on the type of filler implant material. Although FIG. 1 illustrates a single source of curable material 16, in other embodiments, two (or more) sources may be provided. The sources may contain identical curable material compositions; alternatively, the compositions may differ (e.g., a first source may contain bone cement, while a second source contains a mixture of bone cement and bone in-growth material).

As mentioned above, the cannula devices 18a, 18b may be substantially identical, and each includes the outer/access cannula 22a, 22b. The cannula 22a, 22b is provided to be positioned in (or immediately proximate) the target or injection site for delivery of the corresponding cavity-forming device 20a, 20b, as well as curable material. The cannula 22a, 22b preferably is made of a surgical grade of stainless steel, but may be made of known equivalent material(s) that are both biocompatible and substantially non-compliant at the expected operating pressures. The cannulas 22a, 22b each define a proximal region 40a, 40b, a distal end 42a, 42b, and a lumen 44a, 44b (referenced generally), respectively, to allow various equipment such as the cavity-forming device 20a, 20b, a delivery tube 14, one or more stylets (not shown here, but discussed and illustrated with reference to embodiments of FIGS. 4A-4H below), and/or other elements, to pass therethrough.

Surrounding the proximal region 40a, 40b of the cannula 22a, 22b is an handle 46a, 46b for manipulating the cannula 22a, 22b and connecting the cannula 22a, 22b with one or more of the cavity-forming device 20a, 20b and/or the delivery tube 14. In some constructions, the cannula device 18a, 18b may further include a handle connector 48a, 48b serving as a proximal end of the corresponding cannula 22a, 22b. The handle connector 48a, 48b may simply be an extension of the cannula 22a, 22b. Alternatively, the handle connector 48a, 48b may incorporate features forming part of a locking mechanism component of the system 10. For example, the handle connector 48a, 48b may include a luer-lock type of connector, but other known connecting mechanism may be successfully interchanged (e.g., a conventional threaded hole, a threaded locking nut arrangement, etc.). Features of one suitable locking mechanism are described in U.S. Pat. No. 7,922,690, which is incorporated herein by reference in its entirety.

The cavity-forming devices 20a, 20b may be substantially identical and may assume various forms appropriate for forming a void or cavity within bone. In this regard, each of the cavity-forming devices 20a, 20b includes an elongate tubular body 60a, 60b distally connected to or forming a working end 62a, 62b. The elongate body 60a, 60b is sized to be slidably inserted within the lumen 44a, 44b of the corresponding cannula 22a, 22b, and may include one or more tubes, shafts, etc., necessary for operation of the corresponding working end 62a, 62b. Thereafter, a proximal region 64a, 64b of the elongate body 60a, 60b may be connected to or form a cannula connector 66a, 66b. The cannula connector 66a, 66b may assume various forms conducive for selective, rigid attachment to the corresponding handle connector 48a, 48b as described above (e.g., the cannula connector 66a, 66b and the corresponding handle connector 48a, 48b collectively form a locking mechanism), and thus may include or contain a luer-lock threaded fitting. Alternatively, the cannula connector 66a, 66b may be omitted, and depth markings (not shown) included along an exterior of the proximal region 64a, 64b that facilitate desired locating of the working end 62a, 62b relative to the corresponding cannula 22a, 22b as described below.

The working end 62a, 62b may include one or more components appropriate for forming a cavity or void within bone. For example, in some constructions, the working end 62a, 62b may include one or more expandable or inflatable members (e.g., a single balloon, multiple balloons, a single balloon with two or more discernable inflation zones, etc.) constructed to transition between a contracted (e.g., deflated) state in which the working end/balloon 62a, 62b may be passed through the corresponding lumen 44a, 44b, and an expanded (e.g., inflated) state in which the working end/balloon 62a, 62b expands and compacts contacted cancellous bone. In this regard, a size and shape of the working end/balloon 62a, 62b may be predetermined and/or restrained with one or more additional components (not shown), such as internal and/or external restraints. In preferred embodiments the working end/balloon 62a, 62b will be structurally robust, able to withstand (e.g., not burst) at expected inflation pressures and when in contact with bone. Further, the first working end 62a and the second working end 62b may be identical or different.

The working ends/balloons 62a, 62b may be exteriorly coated with a material configured to resist bonding with the curable material being delivered to the vertebra 30. The anti-sticking coating may assume various forms as a function of the selected curable material, and in some embodiments is a silicone coating. Other materials exhibiting aversion to bonding with bone cement are also envisioned, for example, polypropylene. In related embodiments, a thin-walled expandable sleeve constructed of the selected anti-sticking material (e.g., a polypropylene sleeve) may be disposed over the working end/balloon 62a, 62b. Though not shown, one or both of the cavity-forming devices 20a, 20b may include a valve or similar component that operates to selectively seal the working end/balloon 62a, 62b. The coating may also include thermoinsulative properties and/or chemical barrier properties (e.g., silicone coating) that will protect the cavity-forming device(s) during contact with a curable bone cement material such as PMMA, including preventing adhesion and providing thermal protection of a balloon and/or other coated structure(s) during exothermic curing of such material. As such, those of skill in the art will appreciate that the silicone lubricious coating referenced above implicitly provides numerous advantages with respect to providing a system and method of delivering a curable bone cement material (e.g., PMMA) adjacent to and/or contacting a coated expandable member such as a coated (e.g., silicone-coated) balloon of the type described in U.S. Pat. Nos. 8,771,278 and 8,226,657, each to Linderman et al., each of which is incorporated by reference herein.

The cavity-forming devices 20a, 20b each further include one or more additional components connected or operable through the proximal region 64a, 64b for actuating the corresponding working end 62a, 62b. By way of one non-limiting example, each of the cavity-forming devices 20a, 20b may include a source 68a, 68b of pressurized fluid (e.g., contrast medium) for inflating the balloon(s) carried or formed by the corresponding working end 62a, 62b. A hand-held, syringe-type pump may be used as the pressurized source. In other embodiments, a single one of the sources of pressurized fluid 68a or 68b may be provided and employed to inflate both of the working ends/balloons 62a, 62b individually. Appropriate balloon-inflation systems are well known and will readily be apparent to those of skill in the art.

Where provided, the delivery tube 14 is sized for insertion within the lumens 44a, 44b, and defines a distal tip 80 and a proximal section 82. As described below, the delivery tube 14 may be employed to deliver curable material to the target site. Thus, the delivery tube 14 has an outer diameter that is smaller than a diameter of the lumens 44a, 44b; however, the outer diameter of the delivery tube 14 preferably will not be so small as to allow curable material to readily travel around the outside of the delivery tube 14 and back into the corresponding cannula 22a, 22b.

A cannula connector 84 may be coupled to, or formed by, the proximal section 82 of the delivery tube 14. The cannula connector 84 is akin to the cannula connector 66a, 66b described above (e.g., combines with the selected handle connector 48a, 48b to form a locking mechanism), and thus may assume any of the forms previously described. Alternatively, the delivery tube 14, where provided, may form depth markings (not shown) along the proximal section 82 that facilitates desired locating of the distal tip 80 relative to the cannula 22a, 22b during use.

The delivery tube 14 is configured for fluid coupling to the curable material source 16. In some embodiments, a portion of the delivery tube 14 projects proximally beyond the cannula connector 84, and is fluidly coupled to the curable material source 16, for example via an injection connector 86. Alternatively, auxiliary tubing 88 may be provided with the curable material source 16, and fluidly connected to the delivery tube 14 via the cannula connector 84. In yet other embodiments, the delivery tube 14 is omitted, and the curable material source 16 connected directly to the handle connector/proximal end 48a, 48b (e.g., the auxiliary tube 88 is connected to the connector 48a, 48b; or the tubing 88 eliminated and the curable material source 16 (e.g., a syringe) directly coupled to the connector 48a, 48b).

The curable material source 16 may assume various forms appropriate for delivering the desired curable material, and may typically comprise a chamber filled with a volume of curable material and employing any suitable injection system or pumping mechanism to transmit curable material out of the chamber and through the delivery tube 14. Typically, a hand injection system is used where a user applies force by hand to an injector. The force is then translated into pressure on the curable material to flow out of the chamber. A motorized system may also be used to apply force.

Although the system 10 has been described as including the single source of curable material 16, in other constructions, a separate source of curable material 16 may be provided for each of the delivery assemblies 12a, 12b. Similarly, two (or more) of the delivery tubes 14 may be included. Along these same lines, the system 10 may be configured such that the curable material source 16 is directly connected to one or both of the cavity-forming devices 20a, 20b (e.g., the elongate body 60a of the first cavity-forming device 20a may form or terminate at a nozzle proximate (e.g., distal) the working end 62a and through with the curable material may be directly dispensed).

The system 10 and other systems and methods disclosed herein will be useful in performing a wide variety of height restoration and bone stabilization procedures as part of an overall curable material delivery procedure. As such, FIGS. 2A-3B illustrate use of the system 10 in restoring the height of, and delivering curable material into, a target site of a vertebra 100. In general terms, the vertebra 100 includes pedicles 102a, 102b and a vertebral body 104 defining a vertebral wall 106 surrounding bodily material 108 (e.g., cancellous bone, blood, marrow, and soft tissue). The pedicles 102a, 102b extend from the vertebral body 104 and surround a vertebral foramen 110. As a point of reference, systems of the present disclosure may be suitable or readily adapted by those of skill in the art for accessing a variety of bone sites. Thus, although the vertebra 100 target site is illustrated, it is to be understood that other bone sites may be accessed and treated by the system 10 (e.g., femur, long bones, ribs, sacrum, etc.).

The first and second cannulas 22a, 22b may be employed to form first and second access paths to first and second target site locations 120a, 120b. For example, the cannulas 22a, 22b are inserted in a bipedicular fashion through respective ones of the pedicles 102a, 102b and into the bodily material 108. The cannulas 22a, 22b provide access to the corresponding target site 120a, 120b at the open distal ends 42a, 42b thereof. One or more stylets (not shown) may be employed to assist in forming/accessing the target sites 120a, 120b. For example, a series of differently-sized or configured (e.g., sharpened and blunt) stylets may be successively delivered through the respective cannula 22a, 22b to form a channel to the target site 120a, 120b. Alternatively, or in addition, an outer guide cannula (not shown) may be deployed to form an access path for subsequent insertion of the cannulas 22a, 22b.

After the cannulas 22a, 22b are positioned within the bodily material 108 at the desired target sites 120a, 120b, the cavity-forming devices 20a, 20b are assembled to the corresponding cannula 22a, 22b. For example, and as shown in greater detail in FIG. 2B, the elongate body 60a, 60b is slidably inserted within the corresponding cannula 22a, 22b with the respective working end 62a, 62b being distally advanced therethrough. More particularly, with configurations in which the working end 62a, 62b is a balloon or other expandable member format, the working end/balloon 62a, 62b is transitioned to a contracted state (e.g., deflated) so as to be slidably received through the lumen 44a, 44b. The elongate body 60a, 60b is positioned relative to the corresponding cannula 22a, 22b such that the respective working end/balloon 62a, 62b extends distal the corresponding cannula distal end 42a, 42b. For example, where the elongate body 60a, 60b may include depth markings as described above, the appropriate depth marking will be aligned with the corresponding handle connector 48a, 48b (FIG. 1), thereby ensuring that the working end/balloon 62a, 62b is fully deployed or extended beyond the corresponding cannula distal end 42a, 42b. In other constructions, upon connection of the cannula connector 66a, 66b and the corresponding handle connector 48a, 48b, the working end/balloon 62a, 62b is distal the corresponding distal end 42a, 42b and is positioned at the corresponding target site 120a, 120b. Placement of the cavity-forming devices 20a, 20b may be performed simultaneously or consecutively.

Figure 2A:
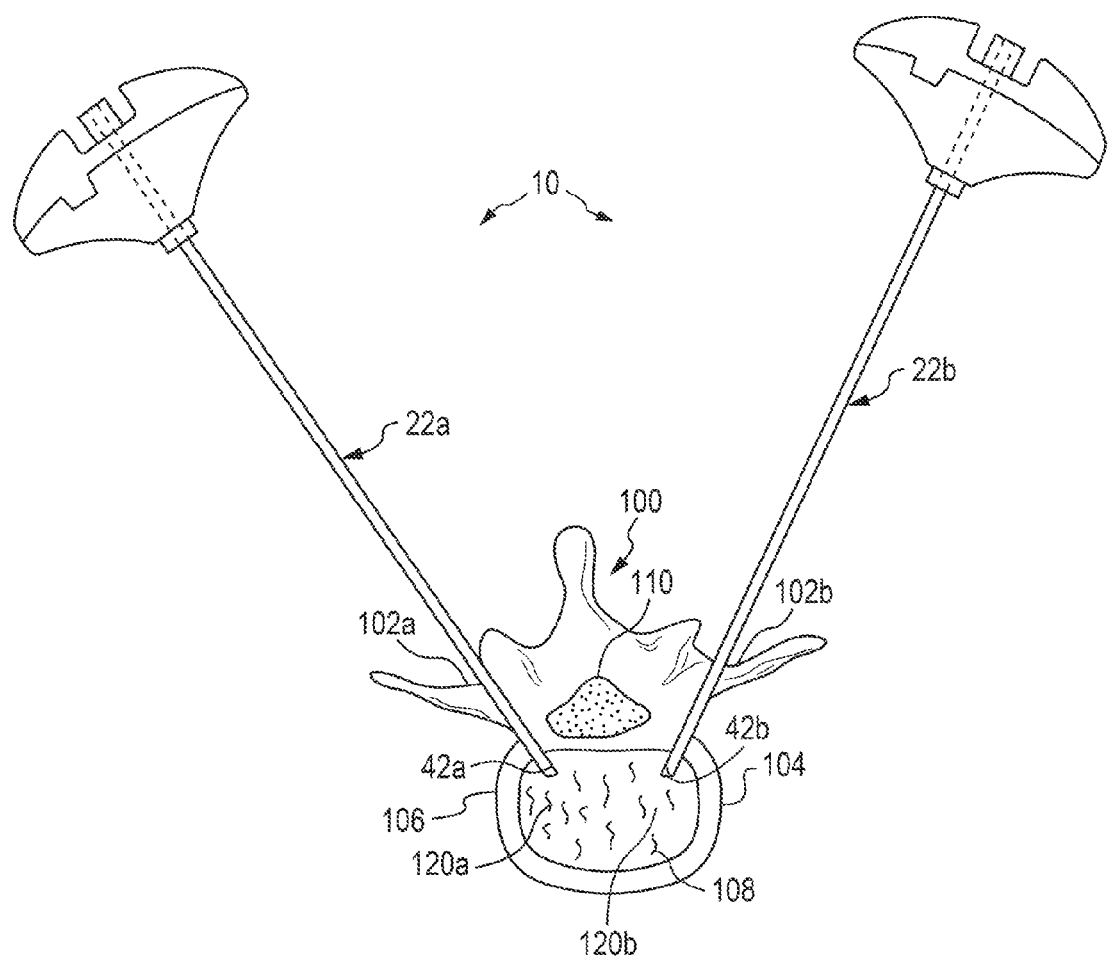
FIGS. 2A and 2B illustrate use of the system of FIG. 1 in performing a height restoration and curable material delivery procedure relative to a vertebra, with the vertebra being shown from a superior perspective.
Figure 2B:
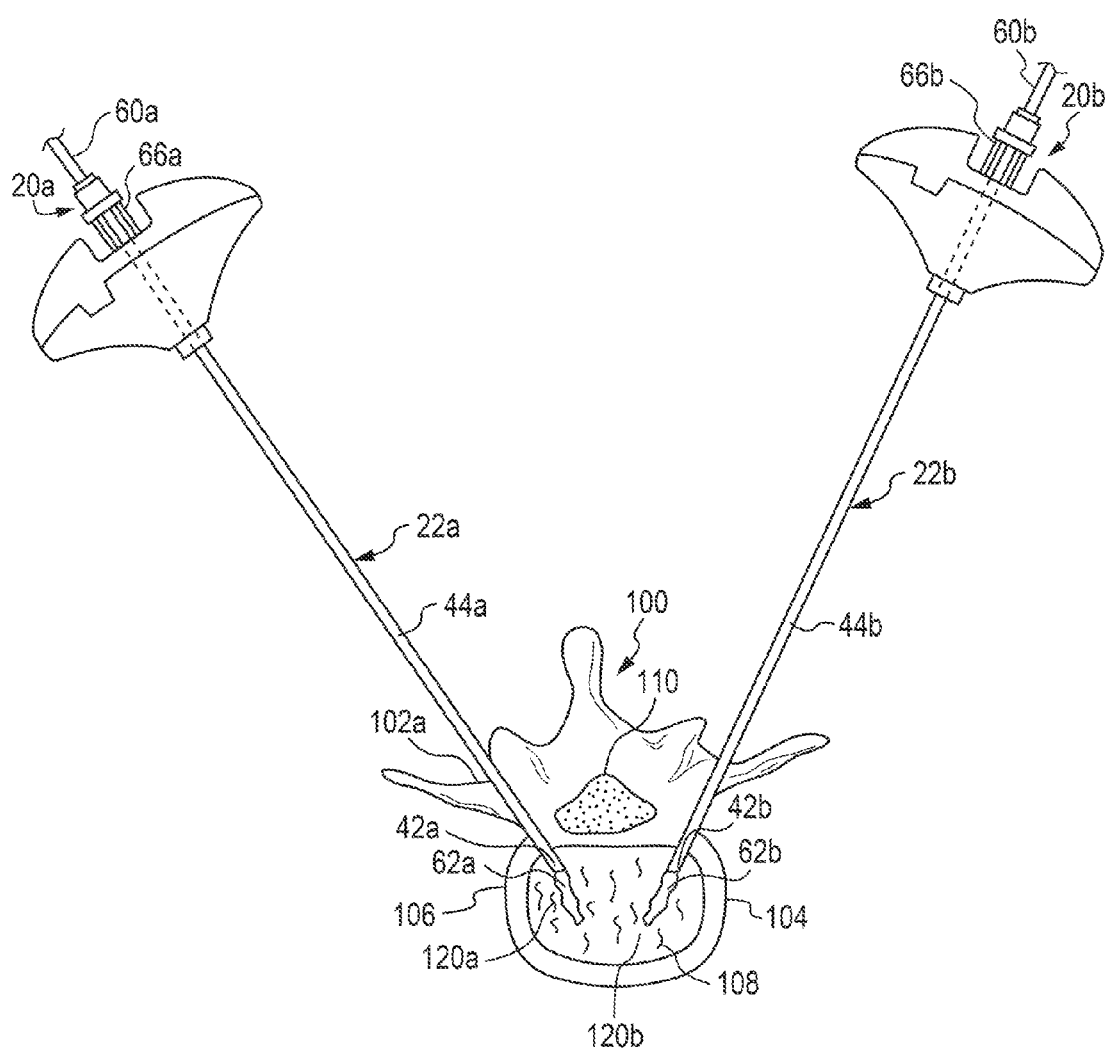
Figure 2C:
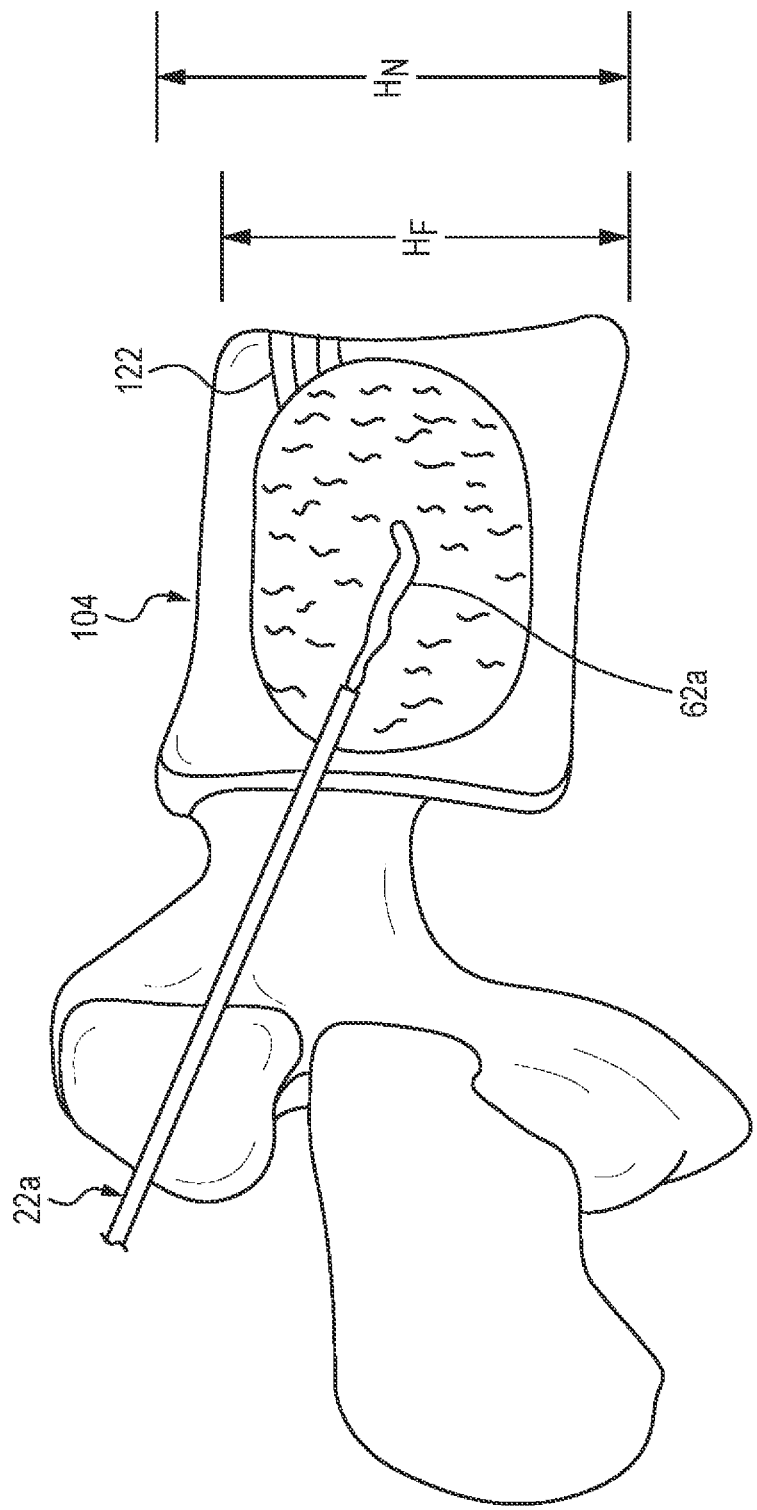
FIG. 2C is a lateral view of the vertebral body of FIGS. 2A and 2B.

As a point of reference, FIG. 2C provides a lateral view of the vertebral body 104 in which the first working end/balloon 62a has been deployed (and in the contracted state). As shown, the vertebral body 104 is fractured (referenced generally at 122) and thus exhibits a fractured height $H_F$ that is less than a natural or native height $H_N$ (designated generally).

Figure 3A:
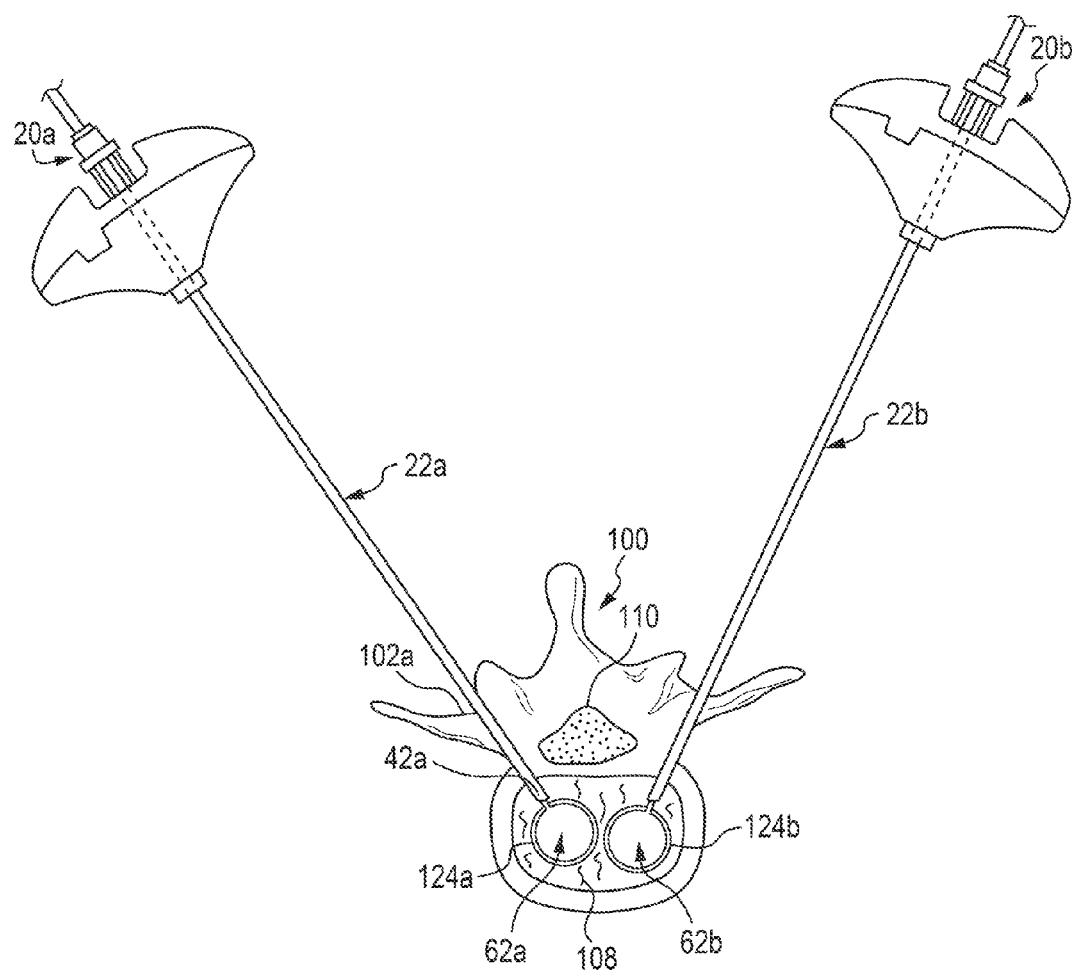
FIGS. 3A-3B illustrate the system of FIG. 1 in further performing the height restoration and curable material delivery procedures with a bipedicular dual-balloon method.
Figure 3B:
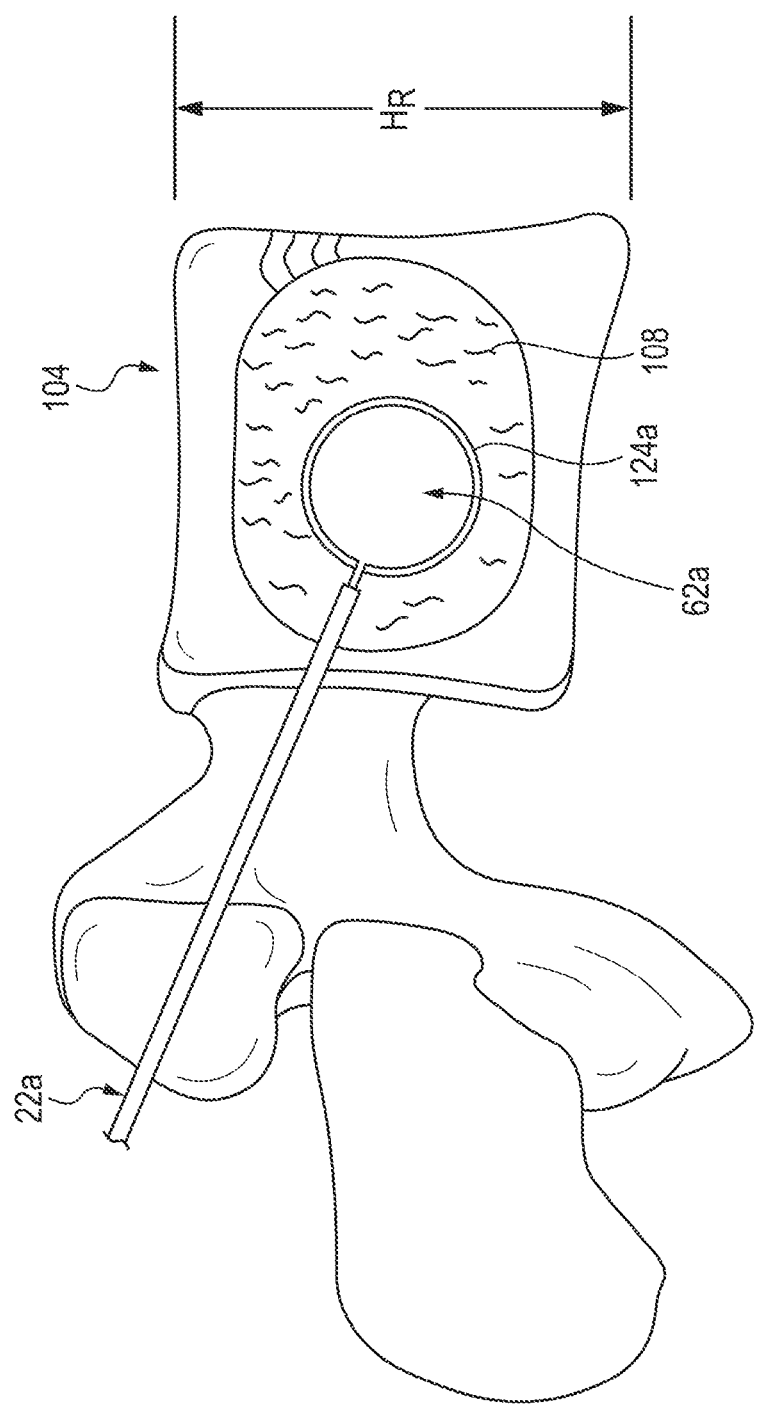

With reference to FIG. 3A, the cavity-forming devices 20a, 20b are operated to cause the corresponding working ends/balloons 62a, 62b to form first and second cavities or voids 124a, 124b, respectively, in the bodily material 108. For example, the working ends/balloons 62a, 62b may be expanded (e.g., inflated) substantially simultaneously. Alternatively, with embodiments in which a single inflation source 68a or 68b (FIG. 1) is provided, the first working end/balloon 62a is inflated and then sealed in the expanded or inflated state. The inflation source 68a or 68b is then fluidly connected to the second working end/balloon 62b and operated to cause expansion thereof. Following expansion of the working ends/balloon 62a, 62b, the expanded working ends 62a, 62b are both supporting the vertebral body 108. In this regard, and as best illustrated in FIG. 3B, expansion of the working ends/balloons 62a, 62b not only forms the cavities 124a, 124b, but also restores or enhances a height of the fractured vertebral body 104. More particularly, a restored height $H_R$ is established that beneficially approximates the natural height $H_N$. The restored height $H_R$ may be the same as, slightly less than, or slightly greater than, the natural height $H_N$ (FIG. 2C); in any event, the restored height $H_R$ will be greater than the fractured height $H_F$ (FIG. 2C).

Returning to FIG. 3A, the second cavity-forming device 20b is then operated to transition the second working end/balloon 62b from the expanded state to the contracted state (e.g., the second balloon 62b is deflated). In the contracted state of the second working end/balloon 62b, the second cavity-forming device 20b may be removed from the second cannula 22b.

Figure 4A:
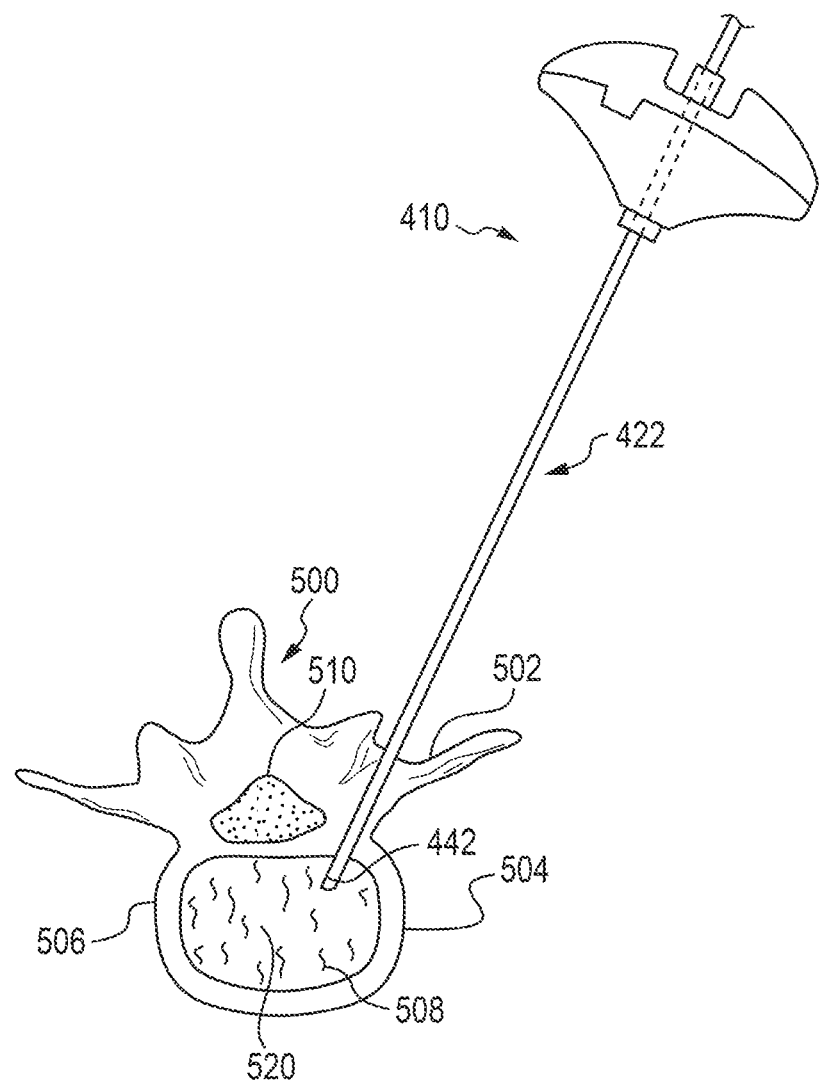
FIGS. 4A-4H illustrate a system and method for transpedicular or parapedicular access providing stylet-guided, generally centralized location of a cavity/void and curable material placement therein.

Other embodiments of a system and method for bone augmentation are described with reference to FIGS. 4A-4H. A system 410 is illustrated in FIG. 4A that may be similar or identical in most respects to the system 10 described above, and corresponding reference numbers should be understood as analogous. Those of skill in the art will appreciate that system components described above with reference to FIGS. 1-3B and in the various incorporated references may be used with the embodiments described below within the scope of the present disclosure. The system includes an access cannula 422 (preferably generally straightline in configuration), which is shown as engaged into a cancellous bone-including region 508 (that may also include marrow and other body material as noted above with reference to FIGS. 2A-3B) of a vertebra 500 via a vertebral pedicle 502 thereof. The distal end 442 of the access cannula 422 has been directed near a target region/site 520 that is generally central within the bone region 508. A portion of the bone region 508 may be at least partially defined by a cortical rim 506 forming a boundary of the anterior vertebral body 504.

The target site 520 may be identified by a physician preparing for a vertebroplasty procedure or other bone-augmentation procedure as discussed herein. Identification of the target site may include generally determining a central location in the cancellous bone portion of the vertebra 500 that will substantially or at least generally support height-restoration and/or structural augmentation that preferably is at least generally symmetrical with respect to the vertebra and particularly with respect to damaged portion(s) thereof. Generally, the target site may be approximately centered within the bone structure. However, the target site is defined more generally as a pre-determined location within a bone structure that may be determined by treating personnel to provide for symmetrical application of force to treat a bone in one or more locations within the bone determined to be most beneficial for the patient.

Figure 4B:
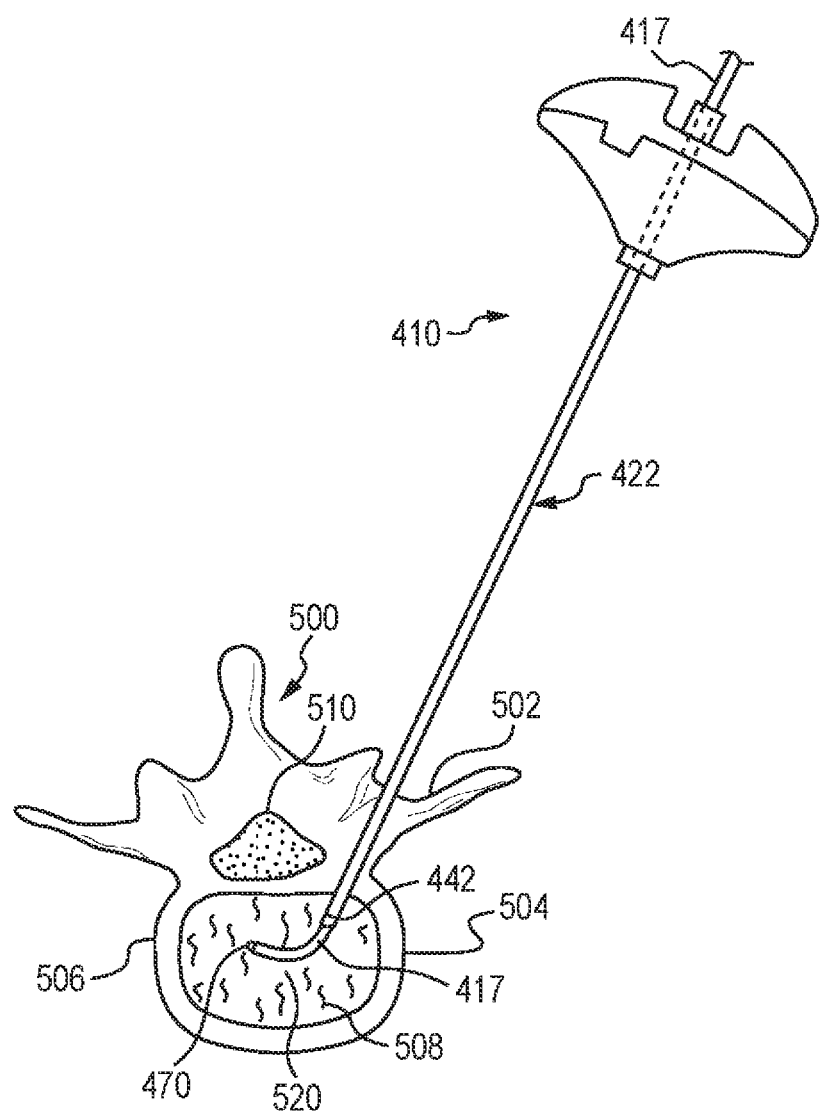

As shown in FIG. 4B, a stylet 470 may be directed through the access cannula 422. The stylet 470 snugly but slidably extends through an overlying delivery tube 417 that preferably is made a flexible polymer having some columnar strength (e.g., polypropylene, PEEK) that will maintain a patent longitudinal lumen upon withdrawal therefrom of the stylet 470. As used herein, "overlying" will be understood by those of skill in the art to describe a coaxial arrangement of the delivery tube 417 around the stylet 470 whereby they may simultaneously be moved longitudinally (e.g., to a target site) while remaining coaxially and longitudinally aligned, whereafter the stylet 470 may be withdrawn from an inner delivery tube lumen defined/bordered/encompassed by the flexible polymeric delivery tube 417. The term "flexible" as used herein will be understood in context by those of skill in the art in describing the delivery tube 417 as being able readily and without crimping or collapsing to assume the curvatures shown and described herein. The delivery tube 417 may include at least one radio-opaque marker (e.g., near its distal end) and/or one or more visual indicia near its proximal end providing for user-observation regarding its distal end position relative to the access cannula of the system. The at least one radio-opaque marker includes that the delivery tube may itself be partially or wholly radiopaque. For example, in certain preferred embodiments, a PEEK (or other polymer) delivery tube 417 may be extruded or otherwise manufactured with Barium in it, such that some or all of the entire tube is radiopaque, obviating the need for other radio-opaque indicia.

The stylet 470 preferably is constructed including a memory metal material having a pre-set curve near its distal end. In this manner, the stylet 470 can be deflected to a generally straight orientation while it is being directed through the access cannula 422. The stylet 470 and the overlying flexible polymeric delivery tube 417 have sufficient length to extend through and be operable beyond the distal end 442 of the access cannula. Thus, as shown in FIG. 4B, in the time and space that the stylet 470 is advanced out of the distal end 442 of the access cannula 422, its pre-set curve is re-asserted such that the stylet 470 and overlying delivery tube 417 curve as they are advanced into the target region 520. The pre-set curve of the stylet 470 may be offset from its distal end sufficiently to provide a generally straightline portion of the stylet distal of its pre-set curve. A proximal-end structure of the stylet 470 may include indicia 471 showing the direction of curvature of the pre-set curve (FIG. 4C).

In certain embodiments, a system may include a plurality of stylets, each having a different pre-set curve. In this manner, a physician may determine a desirable stylet curvature to reach the target region via, for example, one or more transpedicular access sites and select an appropriate stylet. Each stylet may be individually packaged and clearly marked with size and/or curvature, as well as providing other visual indicia of properties of interest to a physician. In use, the physician may determine a desired curvature path between the distal end 442 of the access cannula and the approximate center of the target site (e.g., in the middle of the pre-determined location, which may or may not be generally centered within a bone portion), select a guide stylet including a distal preset curve corresponding to said curvature path from a plurality of guide stylets having different preset curvatures, and insert the selected stylet through the delivery tube 417 before directing the assembled stylet and the then-overlying tube 417 to the target site.

Figure 4C:
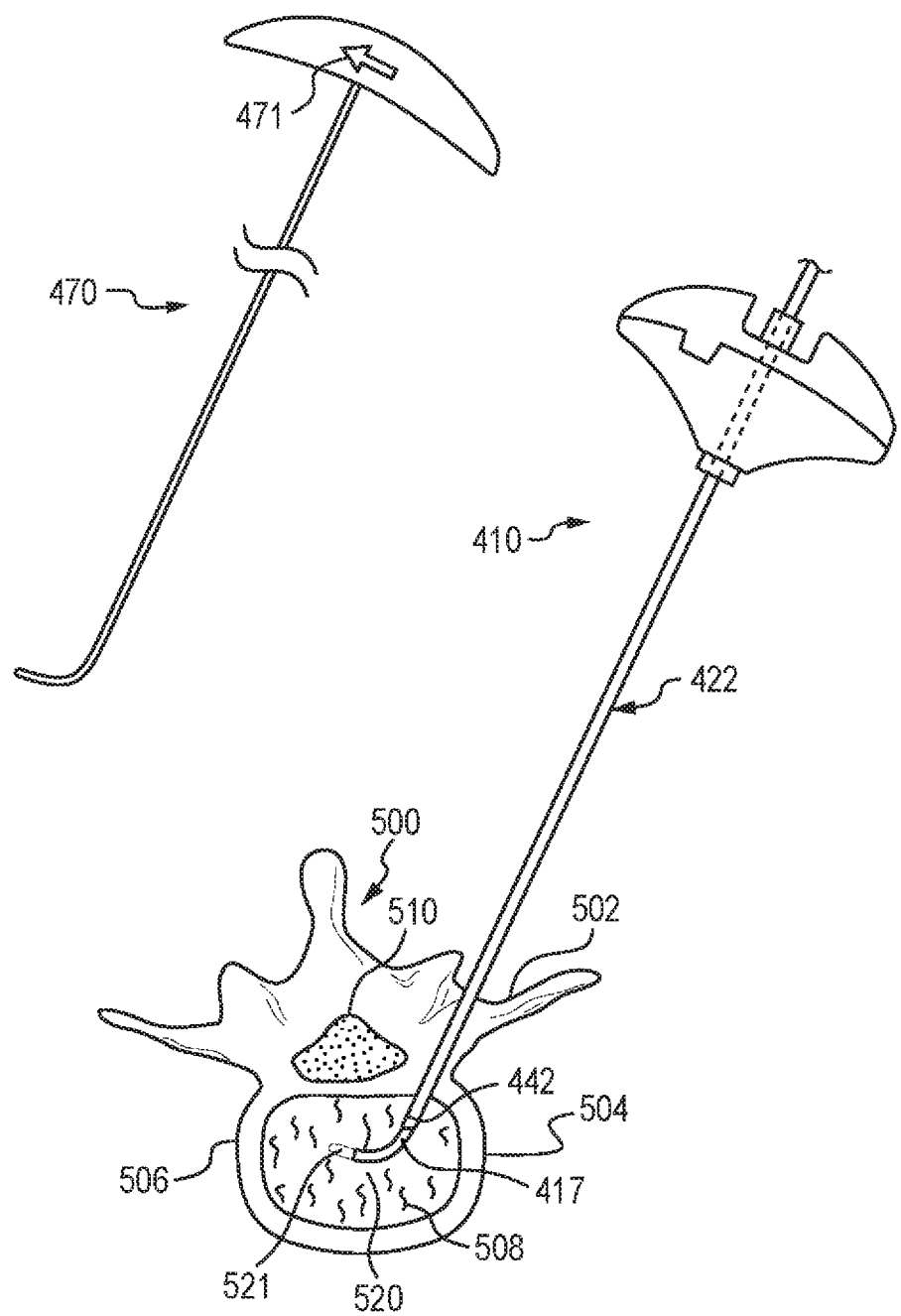
Figure 4D:
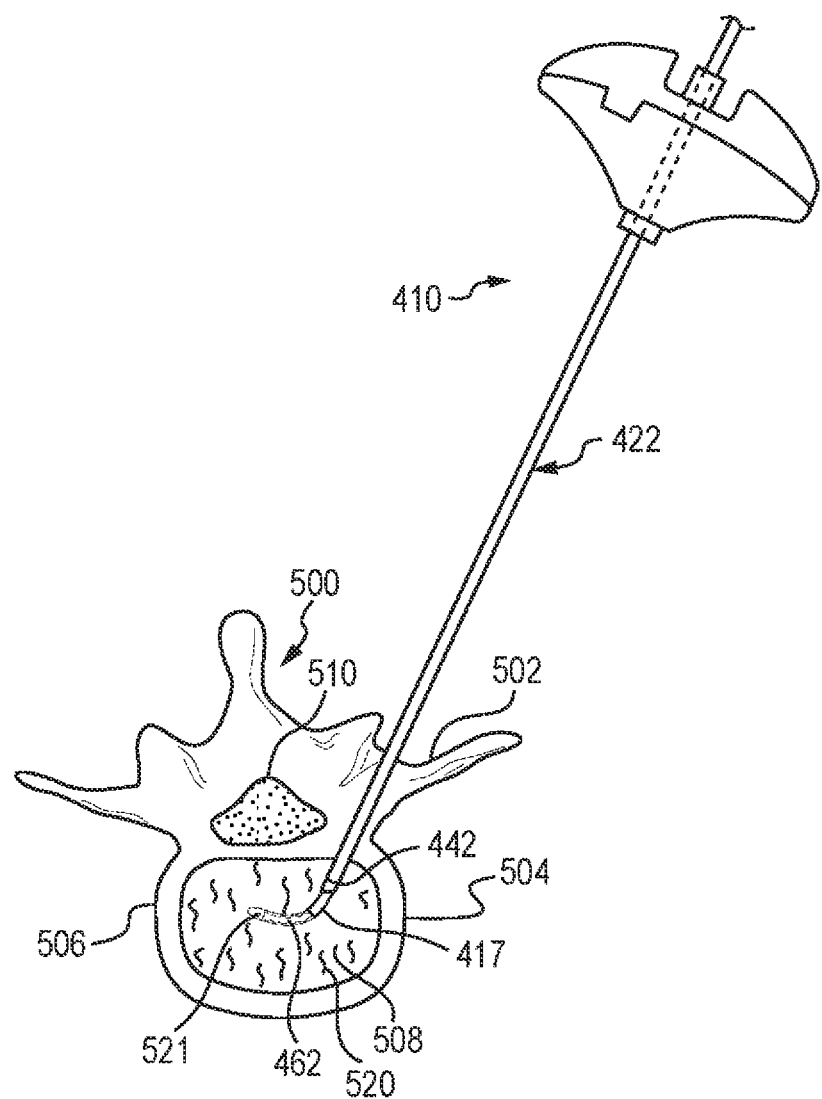
Figure 4E:
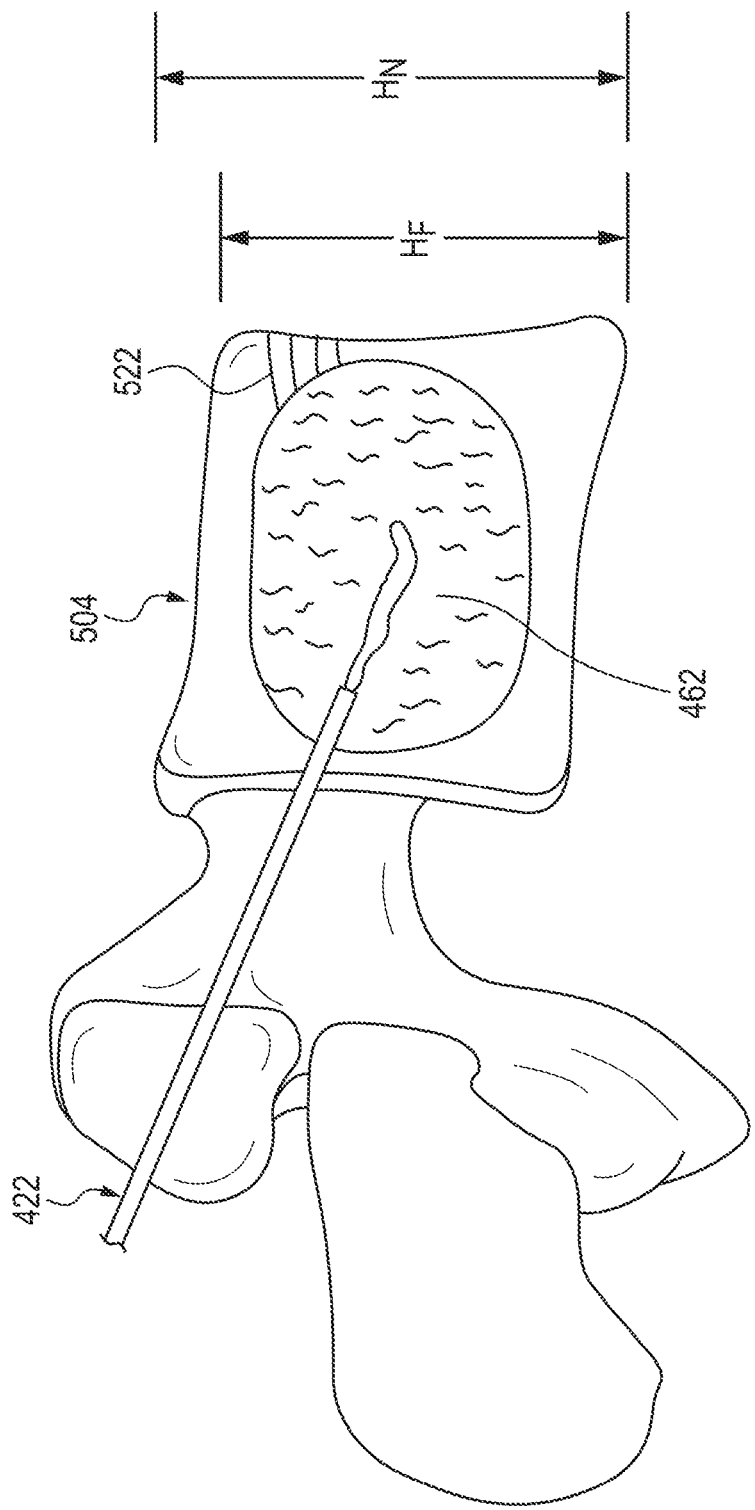

As shown in FIG. 4C, the stylet 470 may be withdrawn from the delivery tube 417 (which is shown as slightly retracted from its furthest extension point) after having created a curved generally tubular path or void 521 in the material 508 in the target region 520. Thereafter, as shown in FIG. 4D, a cavity-forming device, which may include a working end embodied as—for example—a distal balloon 462, may be directed into the path 521 formed by the stylet 470 and now lined by the delivery tube 417 that was formerly overlying the stylet 470 before the stylet was withdrawn. The cavity-forming device(s) may include components analogous to or substantially like those shown in FIG. 1 and discussed with reference to its embodiment including devices 20a and 20b, although the devices shown in the embodiments of FIG. 4C and following primarily show only an expandable member portion such as a balloon and will be understood to have a more flexible inflation-path-shaft than shown for 20a/20b. A wire or other support structure (not shown) may be provided in the cavity-forming device end 462 to enhance its trackability and pushability through/into the path 521. As a point of reference, FIG. 4E provides a lateral view of the vertebral body 504 wherein the working end/balloon 462 has been deployed (and is still in a contracted state). As shown, the vertebral body 504 being treated is anteriorly fractured (referenced generally at 522) and thus exhibits a fractured height $H_F$ that is less than a natural or native height $H_N$ (designated generally).

In one preferred embodiment of a method, the delivery tube 417 may be extended all the way to the end of the cavity/void formed with the stylet 470. Thereafter, the cavity-forming device may be extended through the delivery tube 417 until its working end/balloon 462 contacts the bone at the distal end thereof. This may protect, e.g., a balloon or other distal expandable member of the cavity-forming device from external damage during introductory movement and provide for its placement in a desired location and orientation. In other words, the delivery tube will preferably effectively prevent the balloon from damaging contact (e.g., puncture, cut, tear, or other damage) with and caused by bone structure along the path to the target site. Thereafter, the delivery tube 417 may be withdrawn sufficiently to allow cavity-forming expansion of the working end/balloon 462 as described below. Those of skill in the art will appreciate that one or more of the cavity-forming device, working end/balloon 462 thereof, and the delivery tube may include visual indicia (e.g., markings on the user-held end, radio-opaque indicia at or near the distal end) that enable a user to determine the relative positions of those components to perform a method as described. In this or other embodiments, the inner diameter of the delivery tube 417 and/or the external surface(s) of the cavity forming device(s) may be lubriciously coated (e.g., with silicone, PTFE, and/or another lubricious material).

Figure 4F:
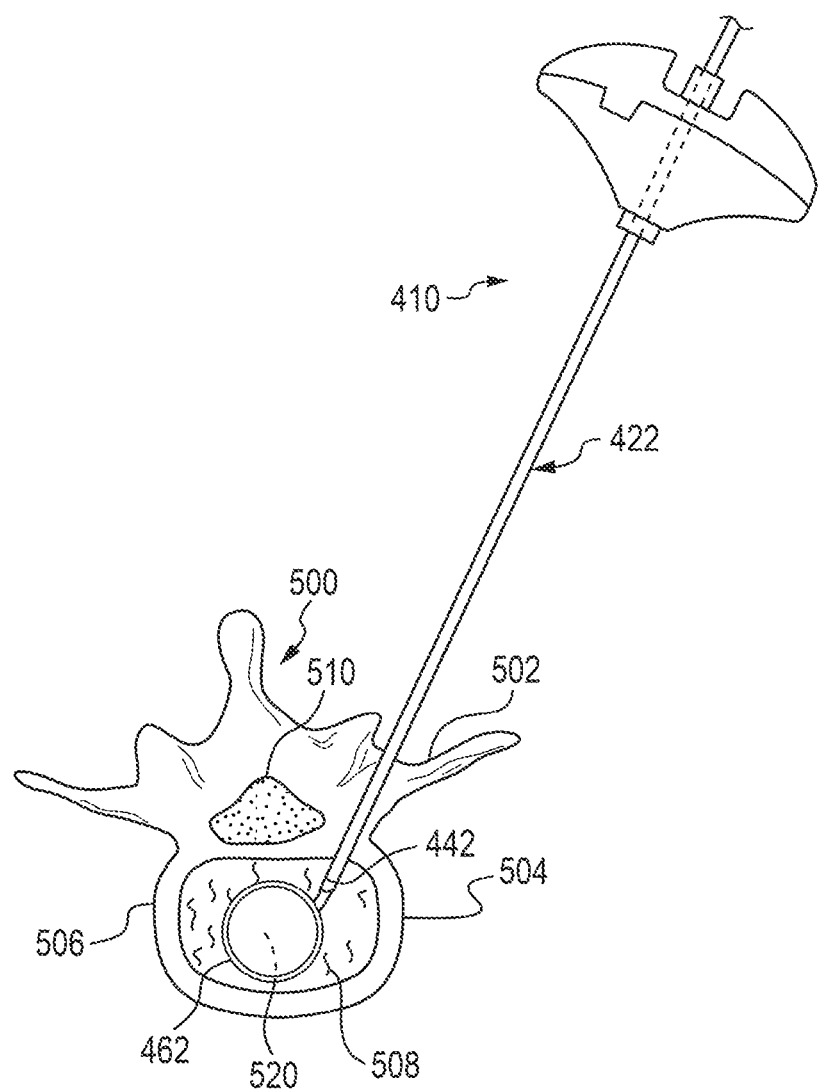
Figure 4G:
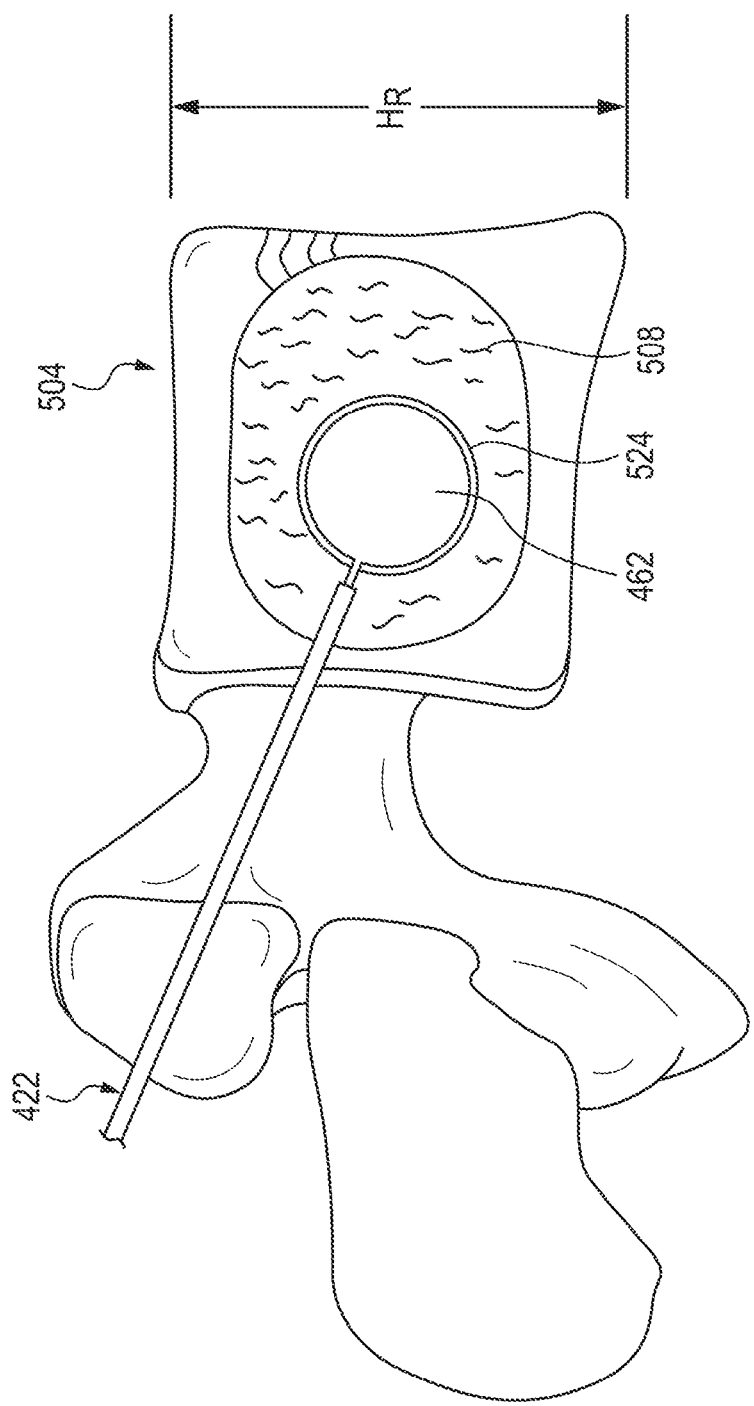

With reference to FIG. 4F, the cavity-forming device may be operated to cause its corresponding working end/balloon 462 to form a (preferably approximately, generally, or substantially centered) cavity/void in the body material 508. For example, the working end/balloon 462 may be expanded (e.g., inflated). As best illustrated in FIG. 4G, expansion of the working end/balloon 462 not only forms the cavity, but may also restore or enhance a height of the fractured vertebral body 504. More particularly, a restored height $H_R$ is established that may beneficially approximate the natural height $H_N$. Such a restored height $H_R$ may be the same as, slightly less than, or slightly greater than, the natural height $H_N$ (FIG. 4E); in any event, any restored height $H_R$ will be greater than the fractured height $H_F$ (FIG. 4E). If desired for fluoroscopic visualization, radio-opaque contrast material may be provided into the cavity, internal to or external of the expandable member. Transpedicular access for kyphoplasty at a target site approximately centered in the cancellous bone may not be easily achievable without the curved stylet approach of the present disclosure. The limits of patient anatomy, the desirability of minimizing procedure time (for the sake of, e.g., cost and patient health), and the desirability of minimizing patient recovery time all provide for advantages of the present methods and systems.

Figure 4H:
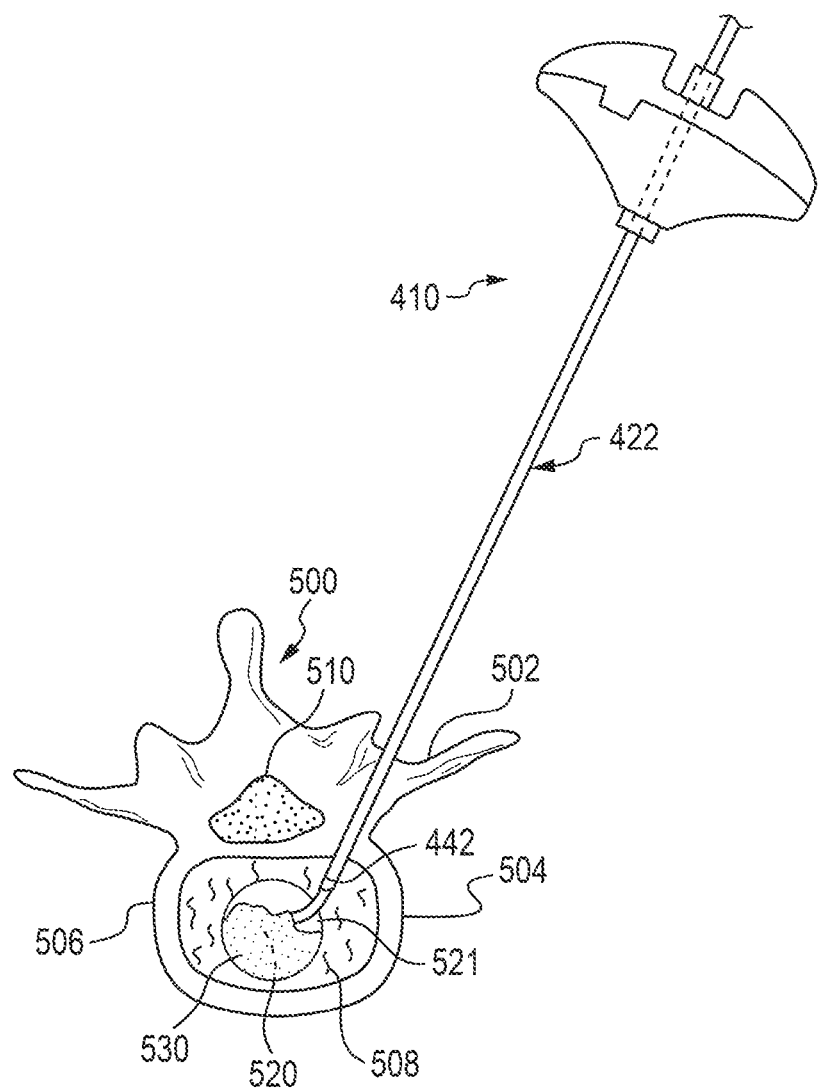
Figure 41:
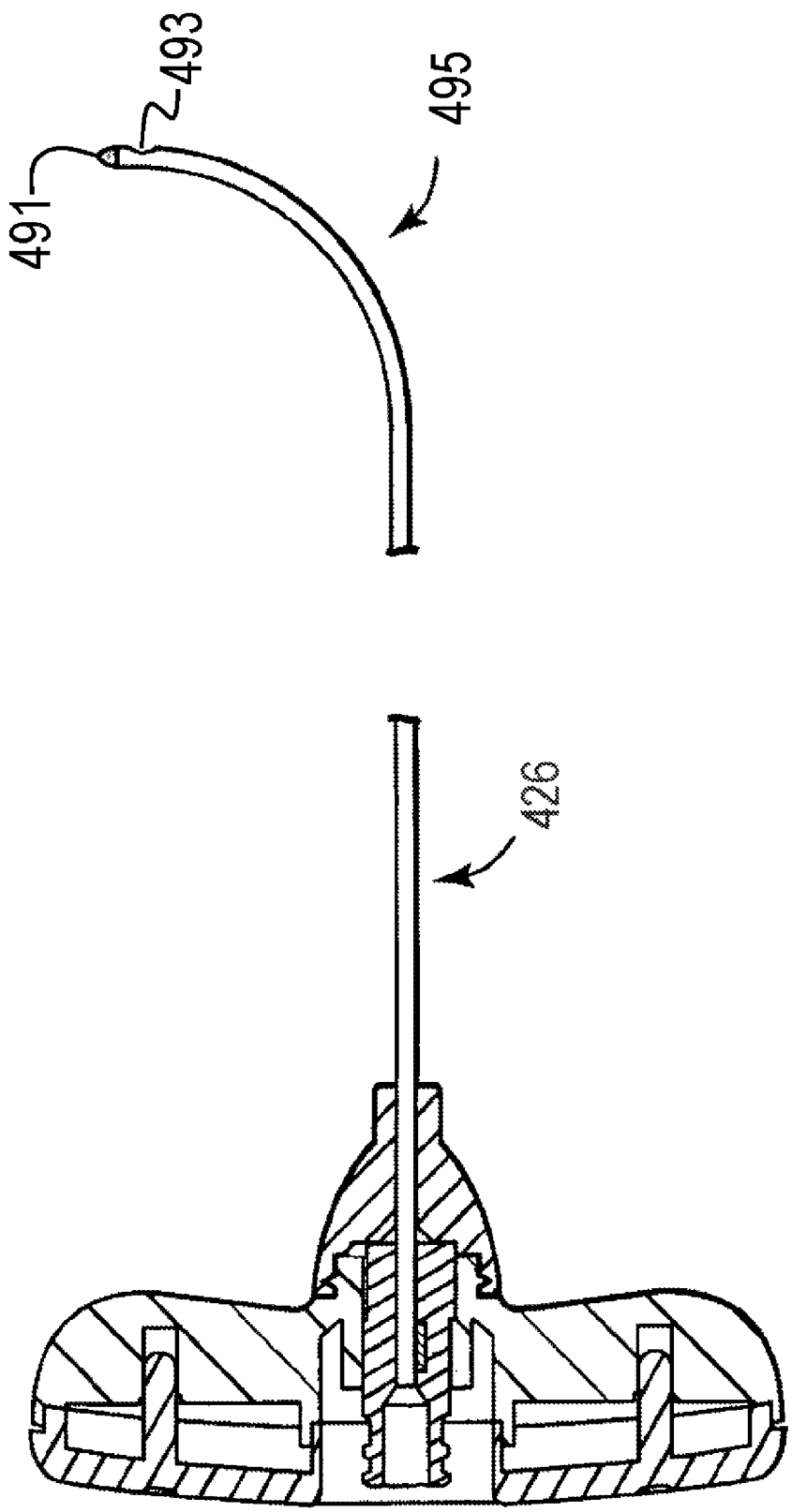
Figure 4J:
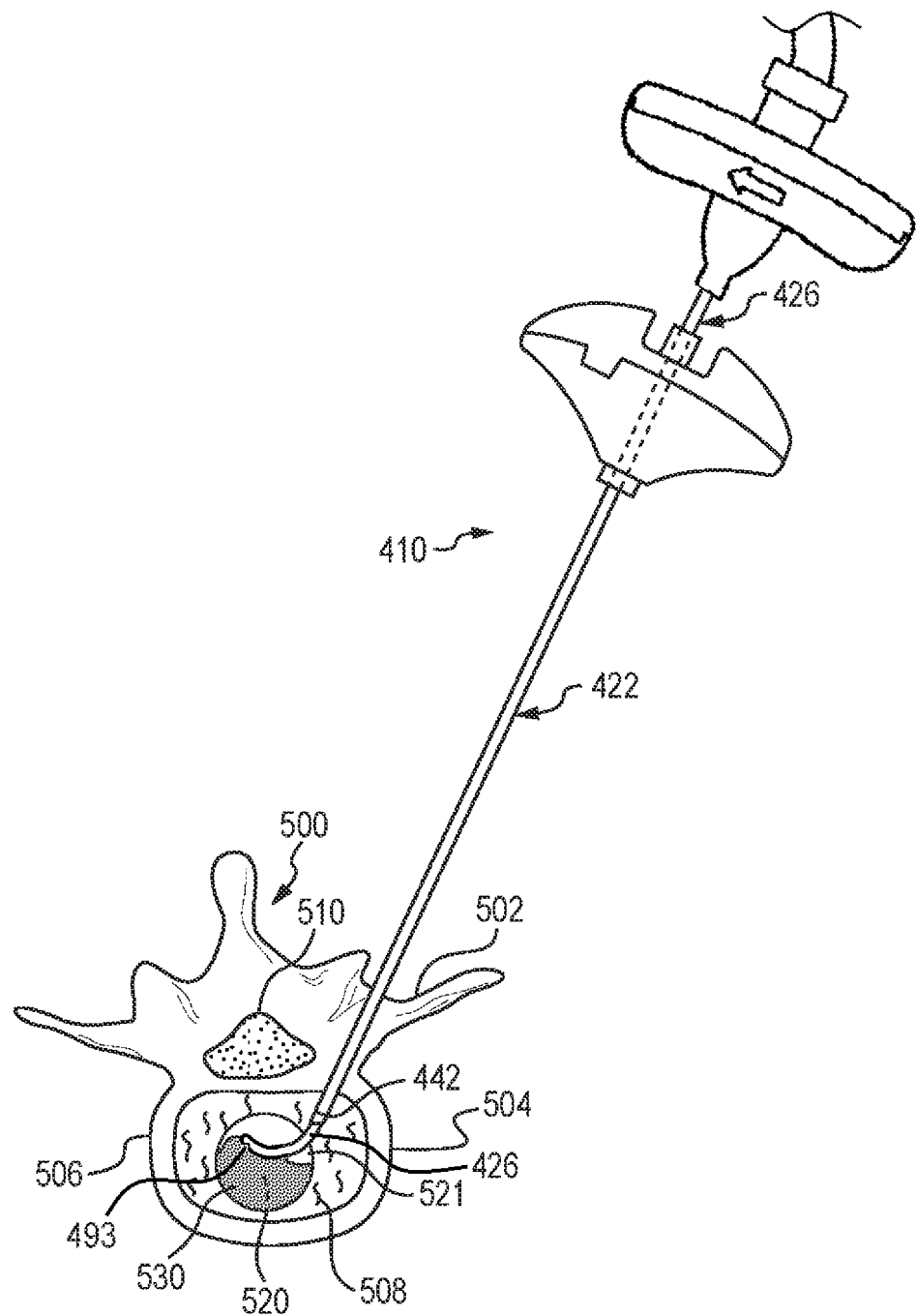
FIG. 4J illustrates another system method for transpedicular or parapedicular access providing stylet-guided, generally centralized location of a cavity/void and curable material placement therein.

Thereafter, the expandable member's working end/balloon 462 may be withdrawn. Then, as shown in FIG. 4H, curable material 530 may be delivered into the cavity via the delivery tube 417. In this or other embodiments, the curable material may delivered in a more targeted manner via a curved delivery cannula 426 (e.g., as shown in FIG. 4I) directed though the access cannula into the cavity 521 (as shown in FIG. 4J). In such an embodiment, the delivery tube 417 may be removed as an intermediate step before introducing the curved delivery cannula 426. Methods and devices for use in introducing curable material via a curved delivery cannula in a manner useful within the presently disclosed systems and methods are disclosed in U.S. Pat. Nos. 7,713,273; 7,799,035, and 8,128,633, as well as U.S. Pat. App. Publ. Nos. 2010/0087828 and 2011/0112588, each of which is incorporated herein by reference in its entirety. It should be understood and appreciated that the "delivery cannula" described therein may include a pre-set curve with structure and function of the curve described herein in reference to a "stylet." However, the term "stylet" as used herein is defined to exclude a delivery cannula that has an internal lumen dimensioned and oriented for delivering curable material, whereas the "stylet" is specifically configured and dimensioned for providing a structure coaxially over/around and along which another device may longitudinally be directed. This definition may, in some embodiments, allow for a stylet that includes a lumen while excluding a stylet lumen in other embodiments, where a typical preferred embodiment will include a stylet with a generally solid cross-section and no continuous longitudinal lumen. It should also be appreciated that the present disclosure enables one of skill in the art to execute the methods of FIGS. 4A-4H in multiple within a single bone structure: i.e., using overlying delivery tube(s) 417 the methods and structures described after the initial set-up shown in FIG. 2A.

In certain embodiments, a delivery cannula may be provided with temperature-dependent multi-curve structure and function as shown and described in commonly-owned U.S. Pat. No. 8,699,884 (already incorporated herein by reference). This cannula may further include an overlying delivery tube 417 and be operated in the manner described above for a stylet, except that the curable material may be introduced through the delivery cannula (e.g., after it is withdrawn; the expandable member is introduced, activated, and withdrawn on its own or with the tube 417; then the delivery cannula—potentially pre-loaded with curable material—is reintroduced through the passage originally created by the stylet).

In some embodiments, which will readily be appreciated by those of skill in the art with reference to the present disclosure and materials incorporated herein by reference, a delivery cannula (e.g., with reference to delivery cannula 426 of FIGS. 4I-4J) may include a closed distal end terminus 491 and a side-facing opening 493 near the terminus 491, where the opening is oriented along an outside surface of the curved portion 495 of the delivery cannula near its closed distal end terminus. It may also include proximal-end indicia 497 that show the direction of distal cannula curvature. The curvature of the delivery cannula may be configured to correspond to the pre-set curve of the stylet 470. In some embodiments, the delivery cannula may be pre-loaded with curable material before the delivery cannula is directed through the guide cannula, in order to decrease procedure time and reduce the likelihood of a bolus during introduction of the curable material.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Although specific terms are employed herein, they are used in a generic and descriptive sense only and not for purposes of limitation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A method for stabilizing a bone structure of a patient, the method comprising steps of:
    identifying a target site for locating an expandable member within a bone structure at a predetermined location,
    directing a distal end of a generally straight access cannula into the bone structure near the target site;
    providing a guide stylet assembly that comprises
        a stylet including memory metal and having a distal pre-set stylet curved portion; and
        an overlying flexible polymeric delivery tube through which the stylet snugly and slidably extends, where the stylet and the delivery tube have sufficient length to extend through and be operable beyond the distal end of the access cannula, and where the pre-set curved portion is held generally longitudinally straight when the stylet is constrained by the access cannula;

directing the stylet and overlying delivery tube simultaneously and coaxially through the access cannula and out the distal end of the access cannula, where the pre-set stylet curved portion, no longer constrained by the access cannula, curves toward and forms a path into the target site as it is extended out of the access cannula distal end;

withdrawing the stylet from the overlying delivery tube; thereafter removing the delivery tube;

directing a coated expandable member in a contracted state via the access cannula into the target site;

expanding the expandable member to form a cavity at the target site; and, thereafter, delivering a curable material into the cavity.

2. The method of claim 1, further comprising, executing steps of:

as part of the step of directing a distal end of a generally straight access cannula into the bone structure near the target site, determining a desired curvature path between the distal end of the access cannula and the approximate center of the target site;

where the desired curvature path is determined by the curvature of the distal preset curved portion; and where the step of directing a distal end of a generally straight access cannula into the bone structure near the target site includes desirably locating and orienting the generally straight access cannula so that, during the step of directing the stylet and overlying delivery tube includes directing a distal end of the stylet and overlying delivery tube to an approximate center of the target site.

3. The method of claim 1, where the access cannula is located and oriented relative to the target site so that the pre-set curved portion of the stylet is oriented to transit from the distal end of the access cannula to approximately the center of the target site.

4. The method of claim 1, where the cavity formed is generally symmetrical within the target site.

5. The method of claim 1, where the cavity formed is generally symmetrical within the bone structure relative to boundaries of the bone structure.

6. The method of claim 1, further comprising, before the step of delivering curable material, removing the expandable member.

7. The method of claim 1, where the step of delivering curable material into the cavity comprises directing a curved delivery cannula through the access cannula into the cavity and directing curable material through the curved delivery cannula into the cavity.

8. The method of claim 1, where the expandable member comprises a silicone-coated balloon.

9. The method of claim 1, where the curable material is delivered through a delivery tube that may be the same or different than the removed delivery tube.

10. The method of claim 1, where the delivery tube comprises at least one radio-opaque marker.

11. The method of claim 1, where the step of delivering curable material into the cavity comprises directing a curved delivery cannula through the access cannula into the cavity and directing curable material through the curved delivery cannula into the cavity, where the delivery cannula curvature is temperature-dependent.

12. The method of claim 1, where the step of delivering curable material into the cavity comprises directing a curved delivery cannula through the access cannula into the cavity and directing curable material through the curved delivery cannula into the cavity, and where the curvature of the curved delivery cannula is about the same as the curvature of the pre-set stylet curved portion.

13. The method of claim 1, further including providing radio-opaque contrast material into the cavity, internal to or external of the expandable member.

14. The method of claim 1, where the stylet includes a distalmost straight length that is distal of the preset curved portion.

15. A system configured for stabilizing a bone structure of a patient, the system comprising:

an access cannula configured for penetrating into a bone structure;

a guide stylet assembly that comprises
a stylet including a distal memory metal pre-set curved portion; and
an overlying flexible polymeric delivery tube through which the stylet coaxially, snugly, and slidably extends, where the stylet and the delivery tube have sufficient length to extend through and be operable beyond the distal end of the access cannula, and where the pre-set curved portion is held generally longitudinally straight when the stylet is constrained by the access cannula;

a silicone-coated expandable member dimensioned and operable for passage through and deployment outside a distal end of the delivery tube in a manner displacing bone material; and a curved delivery cannula configured for delivering curable material into a bone.

16. The system of claim 15, where the delivery cannula includes a closed distal end terminus and a side-facing opening near the terminus, where the opening is oriented along an outside surface of the curved portion of the delivery cannula near the closed distal end terminus.

17. The system of claim 16, further comprising proximal end indicia showing the direction of curvature of the curved delivery cannula.

18. The system of claim 15, further comprising proximal end indicia showing the direction of curvature of the stylet's pre-set curve and indicating when a distal end terminus of the stylet is aligned with and ready to exit the distal end of the delivery tube.

19. The system of claim 15, where the expandable member is embodied 5 as a fluid-inflatable balloon configured to create a cavity by displacing cancellous bone.

20. The system of claim 15, further comprising a curved delivery cannula configured for passage through the access cannula and including a pre-set curved portion corresponding to the curvature of the stylet pre-curved portion, the delivery cannula containing pre-loaded, but not-yet-cured, curable material.

* * * * *